United States Patent [19]
Hoffman, Jr.

[11] Patent Number: 5,860,944
[45] Date of Patent: Jan. 19, 1999

[54] BACK SUPPORT APPARATUS

[76] Inventor: Henry R. Hoffman, Jr., 17222 Club Hill Dr., Dallas, Tex. 75248

[21] Appl. No.: 826,036

[22] Filed: Mar. 28, 1997

[51] Int. Cl.[6] ...................................................... A61F 5/02
[52] U.S. Cl. .................................. 602/19; 2/44; 482/124
[58] Field of Search ................................. 482/121, 122, 482/124; 602/19; 2/44, 92

[56] References Cited

U.S. PATENT DOCUMENTS

| | | |
|---|---|---|
| 401,223 | 4/1889 | Smith . |
| 406,663 | 7/1889 | McKinney . |
| 452,206 | 5/1891 | Aaron . |
| 637,156 | 11/1899 | Potts . |
| 654,173 | 7/1900 | Mendenhall . |
| 658,662 | 9/1900 | Loving ........................................... 2/44 |
| 781,544 | 1/1905 | McMurtry . |
| 807,908 | 12/1905 | Bradstreet ................................. 482/51 |
| 836,802 | 11/1906 | Daniel . |
| 903,403 | 11/1908 | Quick et al. . |
| 1,008,500 | 11/1911 | Thornton . |
| 1,202,851 | 10/1916 | Kelly . |
| 1,371,690 | 3/1921 | Kelly . |
| 1,384,299 | 7/1921 | Brown . |
| 1,409,326 | 3/1922 | Williamson . |
| 1,544,162 | 6/1925 | La Vigne . |
| 1,553,874 | 9/1925 | Nivens . |
| 1,618,273 | 2/1927 | Davidson ................................. 482/124 |
| 1,634,621 | 7/1927 | Martinez . |
| 1,678,584 | 7/1928 | Branson .......................................... 2/44 |
| 2,097,376 | 10/1937 | Marshman ............................... 482/124 |
| 2,613,932 | 10/1952 | Manners .................................. 482/124 |
| 2,906,260 | 9/1959 | Myers ........................................ 602/19 |
| 3,162,442 | 12/1964 | Karlik ...................................... 482/124 |
| 3,295,517 | 1/1967 | Stevens ..................................... 602/19 |
| 4,065,814 | 1/1978 | Fox .......................................... 482/124 |
| 5,186,701 | 2/1993 | Wilkinson ............................... 482/121 |
| 5,259,833 | 11/1993 | Barnett . |
| 5,306,222 | 4/1994 | Wilkinson ............................... 482/124 |
| 5,647,827 | 7/1997 | Gutkowski et al. .................... 482/124 |
| 5,716,307 | 2/1998 | Vadher .................................... 482/124 |

*Primary Examiner*—Richard J. Apley
*Assistant Examiner*—Victor K. Hwang
*Attorney, Agent, or Firm*—Hovey, Williams, Timmons & Collins

[57] ABSTRACT

A back support apparatus includes a pair of shoulder straps and a pair of heel connectors interconnected by a pair of support lines each with a resilient section, and further includes a cover pad with a belt for coupling around the user's waist and for positioning the pad over the user's lower back. In preferred forms, the apparatus includes a pair of spaced tubular guides coupled with the pad for guiding the support lines.

9 Claims, 1 Drawing Sheet

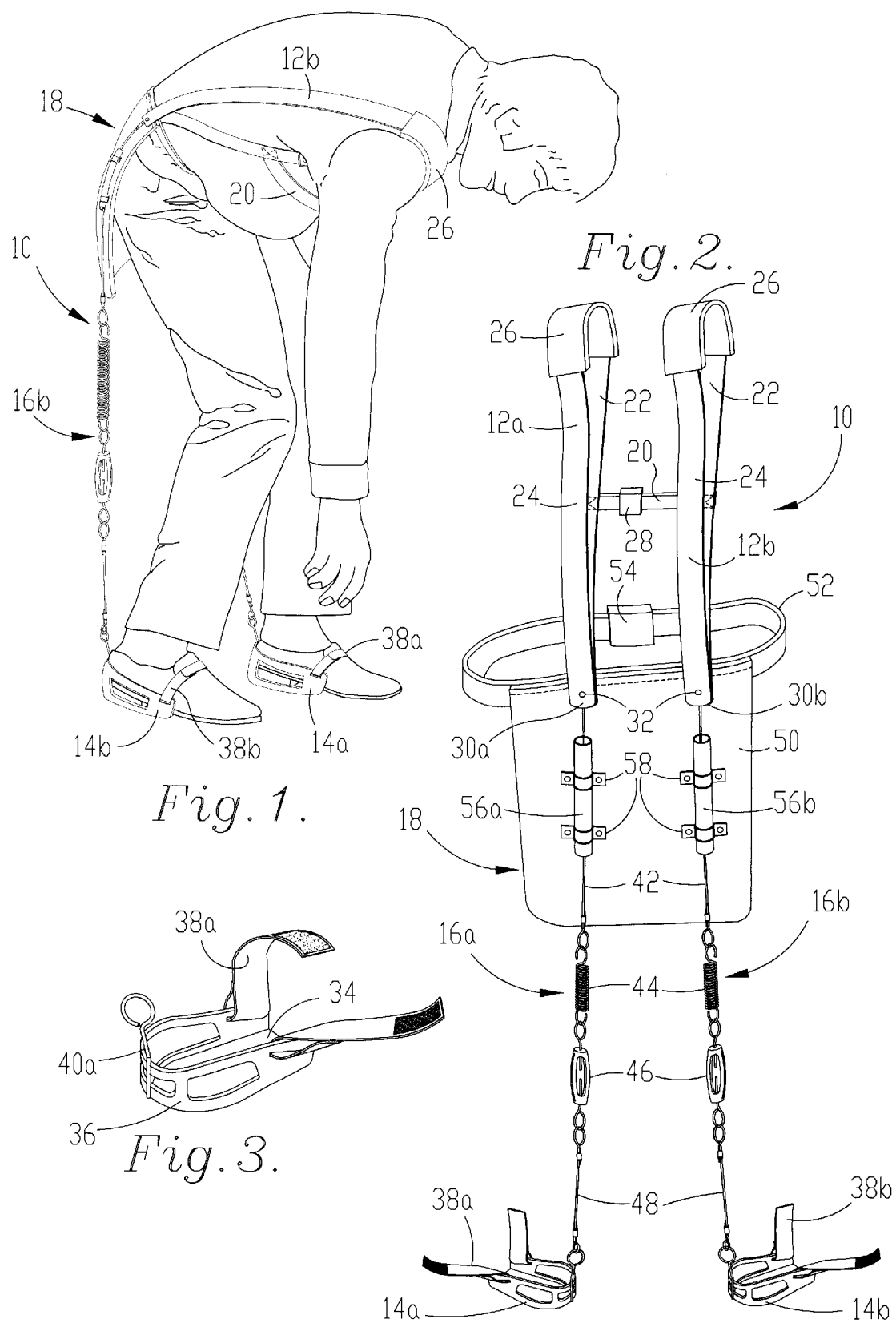

BACK SUPPORT APPARATUS

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention is concerned with the field of back supports as an aid in performing manual labor requiring frequent bending from the waist. More particularly, the invention is concerned with a back support apparatus including a pair of shoulder straps and a pair of heel connectors interconnected by a pair of support lines each with a resilient section.

2. Description of the Prior Art

Some types of manual labor require frequent bending from the waist such as picking crops. This type of labor is particularly stressful on the back muscles sometimes leading to permanent injury.

In the prior art, various devices have been developed for supporting the back during activities requiring frequent bending from the waist. In general, these prior art devices have not been as effective as needed and tend to be mechanically complex or unreliable in use. Accordingly, the prior art points out the need for an improved back support apparatus.

SUMMARY OF THE INVENTION

The present invention solves the prior art problems discussed above and presents a distinct advance in the state of the art. In particular, the back support apparatus hereof is mechanically simple and provides effective support.

The preferred embodiment of the present invention includes a pair of shoulder straps and a pair of heel connectors interconnected by a pair of support lines with each line including a resilient section, and further includes a cover pad having a belt for coupling around the user's waist and for positioning the pad over the user's lower back. In preferred forms, the apparatus includes a pair of tubular guides coupled with the pad and spaced for guiding the lines over the pad. Other preferred aspects of the invention are described herein.

BRIEF DESCRIPTION OF THE DRAWINGS

FIG. 1 illustrates the preferred apparatus of the present invention in service by a user;

FIG. 2 is a rear perspective view of the apparatus of FIG. 1; and

FIG. 3 is a perspective view of the preferred heel connector of FIG. 1.

DETAILED DESCRIPTION OF THE PREFERRED EMBODIMENTS

Referring to the drawing figures, and in particular to FIG. 2, preferred back support apparatus 10 includes shoulder straps 12a and 12b, heel connectors 14a and 14b, support lines 16a and 16b, cover pad assembly 18 and front strap 20. Each shoulder strap 12a,b includes front portion 22, rear portion 24 and shoulder portion 26 presenting a width greater than portions 22, 24 for distributing the load on the shoulders over a greater area. Front strap 20 interconnects front portions 22 of each shoulder strap 12a,b and includes intermediate release buckle 28. Front and rear portions 22, 24 of each strap 12a,b terminate at respective strap ends 30a and 30b and are joined by rivets 32 which also couple strap ends 30a,b with the respective upper ends of support lines 16a,b. Straps 12a,b are not in any way connected to cover pad 18 or belt 52. Straps 12a,b and 20 are preferably composed of leather but could be composed of any material suitable as straps including natural fabrics and synthetic resin materials.

As best viewed in FIG. 3, each heel connector 14a,b is configured to couple with a respective heel of the shoes of the user. In particular, each connector 14a,b includes heel plate 34, upstanding heel brace 36 surrounding three sides of plate 34, connecting straps 38a,b coupled with heel brace 36 on opposed sides thereof and having hook and eye fastening material on the distal ends thereof, and connection eyes 40a and 40b attached to the rearward portion of heel brace 36 for coupling with the corresponding ends of support lines 16a,b.

Support lines 16a,b respectively interconnect strap ends 30a,b and connection eyes 40a,b as shown in FIG. 2. Each support lines 16a,b includes non-resilient, upper cable section 42 connected to a respective strap end 30a,b, resilient section 44, adjuster 46, and lower cable section 48 connected to a respective connection eye 40a,b. Cable sections 42 and 48 are preferably made of wire rope and resilient section 44 is preferably a coil spring. It will be appreciated that other resilient materials could be used including an elastic band, for example. Adjuster 46 is preferably a turnbuckle for adjusting the stretch on resilient section 44 and for thereby adjusting the amount of support assist provided to the user by apparatus 10. This allows apparatus 10 to accommodate users of different height and varying preferences as to the amount of support assist.

Cover pad assembly 18 includes cover pad 50, belt 52 having intermediate buckle 54, and tubular, spaced, parallel line guides 56a,b connected to the outer face of pad 50 by U-shaped brackets 58 riveted to pad 50. Pad 50 and belt 52 are preferably composed of leather but could be made of other materials as discussed above in connection with straps 12a,b. Guides 56a,b are preferably composed of PVC tubing. As shown in FIG. 2, strap ends 30a,b extend into the area of pad 50 in order to prevent abrasion of the user's lower back by strap ends 30a,b.

To use apparatus 10, heel connectors 14a,b are slipped under the respective heels of the user's shoes and connecter straps 38a,b attach snugly over the user's shoes by way of the hook and eye fasteners. Next, shoulder straps 12a,b are placed over the user's shoulders respectively with cover pad 50 in place over the user's lower back. Buckles 28 and 54 are then connected as shown in FIG. 2. Buckles 28 and 54 are preferably configured for adjustability in order to prevent straps 12a,b from sliding off the user's shoulders and for belt 52 to fit snugly about the user's waist. Adjusters 46 are then manipulated for slight tension when the user is standing upright.

As the user bends over as illustrated in FIG. 1, resilient sections 44 stretch and increase their respective biases. Resilient sections 44 carry part of the weight of the upper body and thereby relieve the user's back muscles of some of this load. The farther the user bends over, the greater the assist provided by resilient sections 44. When the user is ready to stand upright, the bias on resilient sections 44 aid in this process also. As discussed above, adjusters 46 can be used to increase or decrease the amount of assist provided by resilient sections 44. During use, line guides 56*a,b* ensure that support lines 16*a,b* do not slip to the side and thereby ensure that the support is provided to the user's back muscles.

Having thus described the preferred embodiment of the present invention, the following is claimed as new and desired to be secured by Letters Patent:

1. A back support apparatus for supporting the back of a user comprising:

a pair of shoulder straps each including a depending portion terminating in a strap end;

a pair of heel connectors each including means for coupling with the heel of the user;

a cover pad including a belt for coupling around the user's waist and for positioning said pad over the user's lower back, said pad presenting an outboard area; and a pair of support lines respectively interconnecting said strap ends and heel connectors with each of said lines including a resilient section, said apparatus further including a pair of tubular guides coupled with said pad and configured for receiving said lines therethrough respectively and spaced for guiding said lines over said area, said shoulder straps being configured so that said strap ends are positioned within the area of said pad and free to shift relative thereto, said resilient sections being positioned between said pad and said connectors.

2. The apparatus as set forth in claim 1, said lines each including adjusting means for adjusting the tension of said resilient section.

3. The apparatus as set forth in claim 2, said adjusting means including means for adjusting the length of said resilient section.

4. The apparatus as set forth in claim 3, said adjusting means including a turnbuckle.

5. The apparatus as set forth in claim 1, said heel connectors including means for coupling with the heels of the user's shoes.

6. The apparatus as set forth in claim 1, said resilient section including a coil spring.

7. The apparatus as set forth in claim 1, said lines including a non-resilient section.

8. The apparatus as set forth in claim 7, said non-resilient section being composed of wire rope.

9. The apparatus as set forth in claim 1, each of said shoulder straps including a front strap portion, said apparatus further including a connecting strap interconnecting said front strap portions.

\* \* \* \* \*